United States Patent
Marshall et al.

(10) Patent No.: US 7,037,275 B1
(45) Date of Patent: May 2, 2006

(54) METHODS AND DEVICES FOR OBTAINING SAMPLES FROM HOLLOW VISCERA

(75) Inventors: Barry J. Marshall, Dalkeith (AU); Agnes Mei-Ling Wong, City Beach (AU)

(73) Assignee: The University of Western Australia, Nedlands (AU)

( * ) Notice: Subject to any disclaimer, the term of this patent is extended or adjusted under 35 U.S.C. 154(b) by 359 days.

(21) Appl. No.: 10/070,238

(22) PCT Filed: Aug. 31, 2000

(86) PCT No.: PCT/AU00/01047

§ 371 (c)(1), (2), (4) Date: Dec. 31, 2002

(87) PCT Pub. No.: WO01/15604

PCT Pub. Date: Mar. 8, 2001

(51) Int. Cl.
*A61B 10/00* (2006.01)

(52) U.S. Cl. .................................................... 600/562

(58) Field of Classification Search ............... 600/562, 600/569, 572, 585, 581, 582, 593, 528, 367, 600/371, 431, 309, 364; 604/164.09, 1, 114, 604/540, 57, 327; 606/2, 7, 27
See application file for complete search history.

(56) References Cited

U.S. PATENT DOCUMENTS

| | | | | |
|---|---|---|---|---|
| 2,773,502 | A | | 12/1956 | Kaslow et al. |
| 3,528,429 | A | * | 9/1970 | Beal et al. ................... 600/367 |
| 3,683,890 | A | * | 8/1972 | Beal ............................ 600/371 |
| 4,481,952 | A | * | 11/1984 | Pawelec ...................... 600/582 |
| 4,735,214 | A | * | 4/1988 | Berman ....................... 600/572 |
| 4,946,440 | A | * | 8/1990 | Hall ....................... 604/164.09 |
| 5,425,377 | A | * | 6/1995 | Caillouette .................. 600/572 |
| 5,738,110 | A | * | 4/1998 | Beal et al. ................... 600/582 |
| 6,475,145 | B1 | * | 11/2002 | Baylor ........................ 600/309 |

FOREIGN PATENT DOCUMENTS

CA   802858   12/1968

* cited by examiner

*Primary Examiner*—Max F. Hindenburg
*Assistant Examiner*—Brian Szmal
(74) *Attorney, Agent, or Firm*—Jagtiani & Guttag

(57) ABSTRACT

A gastrointestinal sampling device that increases the number of epithelial cells removed from the stomach lining without causing additional discomfort to the patient, and which is particularly useful for obtaining samples from the gastric mucus and between the epithelial cells of the stomach. It comprises a drag material (12) for obtaining a gastrointestinal sample and a protective sheath (22) for deployment about the drag material such that the drag material is substantially enclosed by the protective sheath upon removal from the gastrointestinal tract.

23 Claims, 11 Drawing Sheets

PANEL A  PANEL B  PANEL C

METHODS AND DEVICES FOR OBTAINING SAMPLES FROM HOLLOW VISCERA

FIELD OF THE INVENTION

The present invention relates to methods and devices for obtaining samples from hollow viscera. In particular, the present invention relates to methods and devices for obtaining samples from the gastrointestinal tract.

BACKGROUND OF THE INVENTION

In order to accurately diagnose disorders such as ulcers and cancer, physicians and veterinarians often need to obtain biological samples from hollow viscera like the gastrointestinal tract. Methods for obtaining such samples have traditionally involved very expensive and invasive techniques such as gastroscopy. Gastroscopy usually requires the patient to receive an endoscope through the nose or mouth, which then passes through the oesophagus and into the stomach. Once the endoscope tip is in the stomach, biopsy forceps may be inserted through the endoscope such that biopsy material can be taken from the gastric mucus and/or epithelial layer of the stomach. After biopsy, the endoscope is removed from the patient. Each of the steps involved in taking a biopsy may lead to serious patient discomfort, and consequently, gastroscopy is often performed under general anaesthesia or significant sedation. This potentially increases the problems associated with this procedure.

Accordingly, while gastroscopy has the benefit of allowing the operator to inspect the gastrointestinal mucosa, which would allow the detection of ulcerations and/or malignancies, such diseases are uncommon, especially in younger patients. Therefore, it would be preferable not to have to perform gastroscopy unnecessarily, and consequently, there is a requirement in the art for a procedure that is less invasive and more cost-effective, especially when it is necessary to study the normal or abnormal microbiological flora of the gut.

In recent times gastroscopic examination has, to a certain degree, been replaced with less expensive and less invasive techniques, such as digestible pharmaceutical capsules containing extractable strings. These extractable strings are often called gastric strings. To use, the patient holds the free end of the gastric string then swallows the capsule. The string plays out of the capsule as it travels through the patient's oesophagus until the capsule enters the patient's stomach. The capsule then either dissolves or passes through the patient's digestive system, leaving the string within the stomach. After a certain period of time the string is withdrawn, and the end of the string that was in the stomach is subsequently tested for the presence of various microorganisms or for gastrointestinal bleeding. Such a method and device is disclosed in U.S. Pat. No. 3,528,429 and Canadian Patent No 802,858, both of which are fully incorporated herein by reference.

U.S. Pat. No. 3,683,890 discloses a variation of the above device in which the outer dissolvable capsule encloses an inner capsule that is weighted with lead weight. The lead weight enables the string to drag against the inner lining of the stomach to enhance the sampling. The inner capsule is coated on the inside with silicon rubber, which collapses into a flexible bag upon disassociation of the outer capsule; the bag then passes through the pylorus of the stomach into the duodenum. When pulled from the patient, the string detaches from the bag, and the bag with the weight eventually passes with the patient's stool. Whilst this device has advantages over the system described above, the absorptive nature of the string used with this device is not great enough to collect a sufficient number of epithelial cells without dragging against the inner wall of the stomach. Moreover the device is relatively expensive to produce, because two capsules, a flexible bag and a lead weight are required.

Another prior art device has a steel ball that is non-detachably connected to a string. The steel ball promotes the dragging of the string against the inner lining of the stomach, which enhances sampling of epithelial cells. In use, the patient swallows the capsule. When the capsule enters the stomach, it either melts, dissolves or breaks apart and passes through the digestive system. After an indwelling period, the string is pulled out of the stomach, through the oesophagus and out of the mouth. Like other prior art devices, this system has advantages. However, when the string is pulled from the stomach, the steel ball often comes into contact with the gastroesophageal sphincter. This may cause discomfort to the patient, and in some cases, can damage it. This method and device is disclosed in U.S. Pat. No. 2,773,502, the entirety of which is incorporated herein by reference.

The prior art gastric strings described above have all been used for general gastrointestinal sampling, with varying degrees of success. One area for which gastric strings were hoped to be particularly useful was the detection of bacteria such as *Helicobacter pylori*(*H. pylori*). *H. pylori* has been shown to be associated with benign gastric and duodenal ulcers, as well as with gastric cancer, and this organism tends to live under the gastric mucus and between the epithelial cells of the stomach. These types of organisms are most often heavily concentrated in lower portions (i.e. the antrum) of the stomach, and therefore are particularly difficult to sample. Accordingly, the prior art gastric strings described above have had limited success in sampling for these organisms.

While other diagnostic methods are available to detect the presence of bacteria like *H. pylori*, these are known to be non-conclusive. Moreover, since these methods do not actually recover a sample of the bacterium in the stomach, it is possible not only that the organisms being specifically sought will not be present, but that other organisms that these tests can detect will be present. Accordingly, the physician often prefers to culture the organism before prescribing antibiotic therapy.

Thus, as can be seen, there is a real requirement for an inexpensive, non-invasive diagnostic procedure that allows for the recovery of significant samples from under the gastric mucus and between the epithelial cells of the stomach, and which would be particularly useful for sampling organisms such as *H. pylori*.

One device that has recently been proposed for this purpose is disclosed in U.S. Pat. No. 5,738,110. This device includes a gelatin pharmaceutical capsule that contains a sampling string made of a mixture of bees' wax and mineral oil. The applicant of this patent contends that the sampling string used is sufficiently different to those used previously to overcome the problems highlighted above. However, one major problem that this device does not solve is the problem of bacterial contamination of the sampling string on removal from the gastrointestinal tract.

In all of the prior art devices described above, the gastric string passes through the mouth and oesophagus on withdrawal. However, none of these devices protects the gastric string from contamination upon its withdrawal from the stomach. This is a potential problem, as the mouth and oesophagus usually have a high background level of commensal flora, which can cause significant contamination of the string. This problem is especially relevant when trying to detect *H. pylori*, which is a very fastidious organism that is slow to culture. Consequently, the commensal organisms which contaminate the string often outgrow the *H. pylori* in culture to such a degree that detection of *H. pylori* is difficult if not impossible.

Thus, based upon the foregoing, it would be readily apparent to those of skill in the art that there is a need for a relatively inexpensive gastrointestinal sampling device that enhances sampling without contributing to the discomfort of the patient. Moreover, there is a requirement for a device that is capable of sampling microorganisms from specific regions of the gastrointestinal tract without becoming contaminated with microorganisms from other regions. Accordingly, the present invention attempts to overcome or at least alleviate some of the problems highlighted above, especially those related to the contamination problems discussed.

SUMMARY OF THE INVENTION

The present invention is directed towards a gastrointestinal sampling device that increases the number of epithelial cells removed from the stomach lining without causing additional discomfort to the patient, and which is particularly useful for obtaining samples from under the gastric mucus and between the epithelial cells of the stomach. To these ends, the present invention provides a gastrointestinal sampling device comprising:
  a drag material for obtaining a gastrointestinal sample; and
  a protective sheath for deployment about the drag material such that the drag material is substantially enclosed by the protective sheath upon removal from the gastrointestinal tract.

The present invention further provides a gastrointestinal sampling device for the diagnosis of certain gastrointestinal pathogens comprising:
  a drag material for obtaining a gastrointestinal sample; and
  a protective sheath for deployment about the drag material such that the drag material is substantially enclosed by the protective sheath upon removal from the gastrointestinal tract.

The present invention further provides a method of gastrointestinal sampling comprising the steps of:
  swallowing a gastrointestinal sampling device comprising a drag material and protective sheath;
  allowing sufficient time for said drag material to obtain said gastrointestinal sample;
  withdrawing said drag material such that on withdrawal said protective sheath encloses said drag material; and
  recovering said gastrointestinal sample for testing.

Preferably, the gastrointestinal sampling device further includes a capsule for carrying the drag material and protective sheath.

Preferably, the protective sheath is deployed about the drag material by movement from the retracted position to an extended position. Preferably, the retracted position of the protective sheath is held in place by edible glue.

Preferably, the drag material is folded within the capsule, and has a weight for assisting with the extension of the drag material in the stomach of a patient.

The present invention further provides a method of manufacturing a gastrointestinal sampling device comprising the step of encasing a drag material and protective sheath in a capsule.

Throughout the description and claims of this specification, the word "comprise" and variations of the word, such as "comprising" and "comprises", means "including but not limited to" and is not intended to exclude other additives, components, integers or steps.

DETAILED DESCRIPTION OF THE INVENTION

Without affecting the generality of the invention described above, the present invention will now be described with reference to the accompanying drawings.

Figure 1:
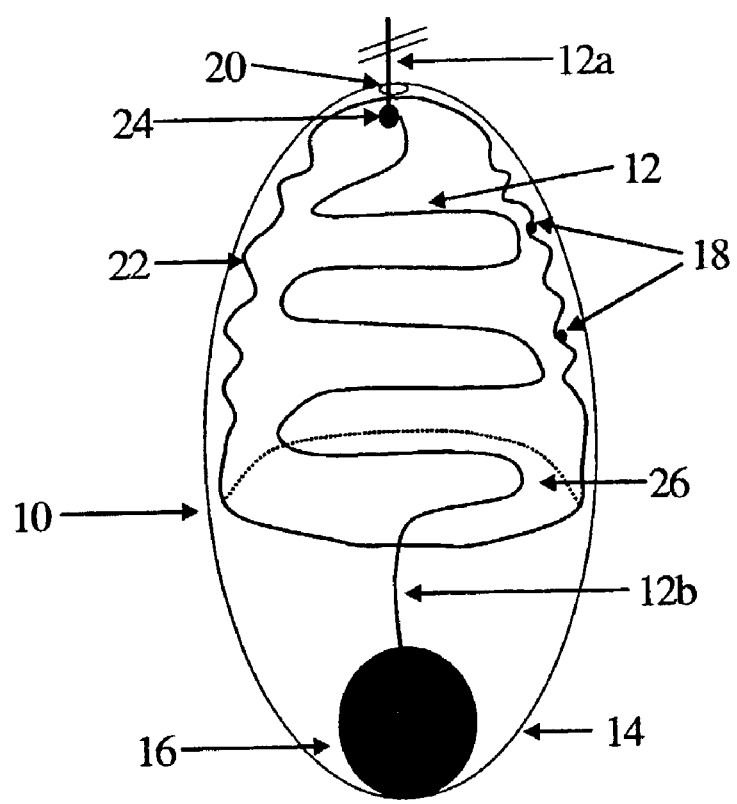
FIG. 1 is a front side view of the gastrointestinal sampling device.

FIG. 1 illustrates a device according to one embodiment of the present invention. A gastrointestinal sampling device 10 includes a capsule 14. The capsule 14 can be of any size. Preferably, the capsule 14 is no more than 2 cm in length and 0.9 cm in diameter. More preferably, the capsule 14 is between size 0 and size 000 ie a size that a patient could easily swallow. The capsule 14 contains drag material 12, which comprises two portions 12*a* and 12*b*.

Capsule 14 may or may not be dissolvable, and may comprise more than one piece or part. If the capsule 14 is dissolvable, it is preferable that it is constructed of gelatine or other pharmaceutically acceptable material that readily dissolves when subjected to stomach acid. If the capsule 14 is constructed of non-dissolvable material, it is preferable that the material used is either plastic or some other non-toxic material, which will readily pass through the digestive system. Furthermore, if the capsule is non-dissolvable it is preferable that it is composed of at least two parts joined together with water-soluble glue. As described in more detail below, this construction will allow the capsule to separate in vivo such that the drag material 12 is released.

The gelatine capsule 14 may be substituted with a hot gelatine dip, which encases sterilised drag material 12. When the gelatine cools, the drag material 12 can be formed as a capsule surrounded by gelatine. The gelatine used for the hand dipped capsule embodiment of the device 10 may be softer than the gelatine used in standard gelatine pharmaceutical capsules.

The portion 12b is preferably situated adjacent to one end of the capsule 14. Both portions of drag material 12 may be composed of the same material for their entire lengths, or alternatively, portions 12a and 12b are made of different material(s). Whether different material is used for both portions or not, it is preferable that at least portion 12b is malleable, yet firm enough to maintain its mass against moderate resistance. Accordingly, portion 12b may be composed of any material which fits this description; however, it is preferable that it is composed of material selected from the group consisting of absorbent string, sampling cloth, steel wool and chain link material or a combination thereof. Most preferably, the drag material 12 per se or portion 12b is absorbent string such as nylon or cotton string.

The lengths of portion 12a and 12b will depend upon the size of the individual or animal being tested, as well as the sample site. Preferably, portion 12b is at least 12 cm in length.

In one preferred embodiment, portion 12b is a malleable sampling material such as absorbent string or sampling cloth, while portion 12a is either absorbent string or like material. Portion 12a runs through an opening or perforation 20 in the capsule 14, while portion 12b is located within one end of the capsule 14. As shown in FIG. 1, the majority of portion 12a runs through the opening or perforation 20, while the rest of portion 12a is inside capsule 14 and attached to portion 12b. Portion 12b is tightly wound or randomly packed in cocoon-like fashion within capsule 14.

In another preferred embodiment, portion 12b is wound such that a weight 16 at the end of portion 12b is located on the exterior of the winding. Such an arrangement allows for portion 12b to be pulled out of the capsule 14 without binding or snagging. Portion 12b can also be installed in the capsule 14 by randomly packing within the capsule 14. Further, portion 12b can also be installed in capsule 14 by packing it within the capsule in accordion-like fashion.

Surrounding portion 12b, and the segment of portion 12a that is inside capsule 14, is a protective sheath 22. The protective sheath 22 may be made of any suitable material known, including plastic, cloth or finely knitted metal. Preferably, the protective sheath 22 is plastic, and made from either polyethylene or polythene film. Protective sheath 22 may also be of any length or diameter, but generally depends upon the size of portion 12b used. For example, the sample site in the gastrointestinal tract will dictate the length of portions 12a and 12b required. As the role of protective sheath 22 is to cover the majority of portion 12b on withdrawal, it must be of sufficient length to accomplish this. Preferably, protective sheath 22 is approximately 10 cm long.

In FIG. 1, protective sheath 22 is shown concertinaed in one end of capsule 14 with portion 12b tightly wound or randomly packed in cocoon-like fashion. Protective sheath 22 is preferably an open-ended tube, wherein the open end 26 is distal to the hole or perforation 20 in the end of capsule 14. The closed end of protective sheath 22 is in close proximity to, or in contact with, the region of capsule 14 which contains the hole or perforation 20. In this configuration, portion 12a passes through the protective sheath 22 as depicted in FIG. 1. In order to stop portion 12b being pulled through the hole or perforation 20 upon withdrawal or during swallowing, it is preferable to have a protective sheath retainer 24 present. The protective sheath retainer 24 may be a simple knot in portion 12b, or it may be any other means by which the passage of portion 12b through the protective sheath 22 can be stopped. For example, protective sheath retainer 24 may be a small plastic or metallic bead.

As shown in FIG. 1, the terminal end of portion 12b, ie the end not attached to portion 12a, is preferably attached to a weight 16. The weight 16 can be permanently or detachably fixed to portion 12b. Weight 16 may be constructed of any suitable material, and be of any suitable size. The role of weight 16 in use is to assist in the deployment of portion 12b once capsule 14 dissolves or separates. Preferable, the weight 16 is made of non-toxic metal as in use it may be desirable to increase the effectiveness of the sampling by applying a magnetic force to the weight 16 to position it as required.

As described in more detail below, it is preferable that in use the protective sheath 22 does not deploy at the same time as portion 12b. In order to effect this it is preferable that protective sheath 22 is halted in its deployment for a period of time considered sufficient to allow portion 12b to extend, and come into contact with the sample site. A person skilled in the art will appreciate the significance of this time delay, as well as be able to determine what the period of time should be. In one preferred embodiment, this delay in deployment is effected with the use of glue 18. A bead of glue 18 is attached to the protective sheath 22 such that protective sheath 22 can not expend to its complete length for approximately 10 minutes after the capsule 14 has dissolved or separated. Preferably, glue 18 is water-soluble glue that is non-toxic and edible.

Figure 2:
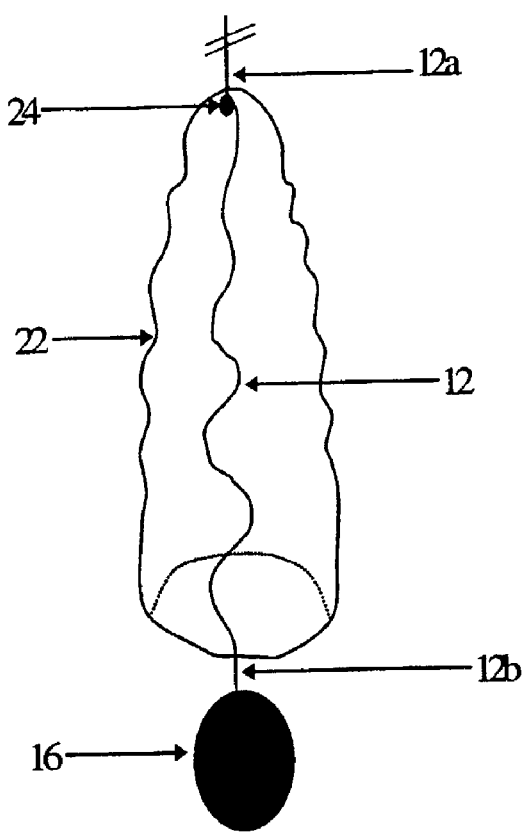
FIG. 2 is a diagrammatic view of the protective sheath in extended form.

FIG. 2 depicts the device of FIG. 1 in fully deployed form, illustrating the protective sheath 22 in greater detail.

In one preferred embodiment of the preferred invention, the length of portion 12b is increased and the width is decreased such that the same volume of material fits within the capsule 14. Thus, for example, instead of using a length of 20 cm and a width of 2 cm for portion 12b, the length of portion 12b would be 40 cm and the width would be 1 cm. The advantage of an elongated portion 12b is that it is better able to collect and facilitate detection of any bleeding that might occur within the entire length of the stomach including the gastro oesophageal junction.

Figure 3:
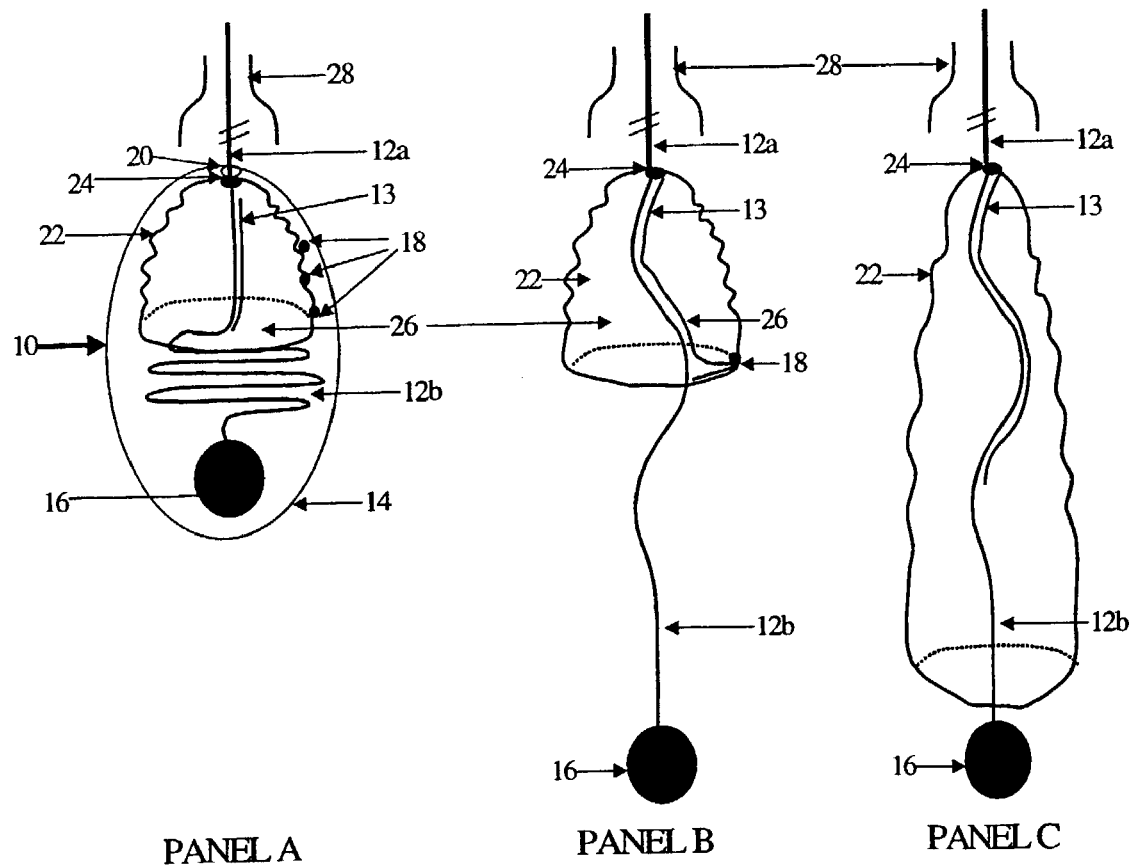
FIG. 3 is a diagrammatic representation of the device in use. Panel A shows the device in situ in the stomach before the capsule dissolves. Panel B shows the capsule dissolved, the drag material deployed and the protective sheath retracted. Panel C shows the device being removed with the protective sheath deployed such that it encases the drag material.

One especially preferred embodiment of the present invention is depicted in FIG. 3, and is shown as it is intended to be used. The capsule 14 is constructed from gelatine. A fasting patient swallows the capsule 14 with a drink of water. Preferably warm water is used. As the capsule 14 is swallowed it pulls drag material 12a down the oesophagus into the stomach with it. Within approximately 5 minutes of entering the stomach, the warm moist environment causes the capsule 14 to dissolve. At that time, by its own weight, or by the action of the weight 16 and by posturing the patient, portion 12b deploys from the protective sheath 22 and unrolls 12 to 15 cm within the stomach. At this time, because the protective sheath 22 is held in place by water-soluble glue 18 it does not deploy. The patient remains in the vertical position while portion 12b deploys and comes into intimate contact with the adjacent mucus lining of the stomach. Contact with the mucus layer can be enhance by applying a magnet to the abdomen, thus pulling portion 12b or weight 16 composed of a magnetic substance tightly against the gastric mucosa. Portion 12b then collects mucus from the gastric wall and remains in this position for up to one hour. The mucus contains many *H. pylori* organisms. Other organisms, which might have been swallowed with a capsule 14, are by now killed by the gastric acid present in the stomach. During this time also, the drink of water, which was taken with the capsule 14, has passed into the intestine.

Accordingly, the stomach is rather dry with both adjacent walls in contact with portion 12b, thus loading it with mucus. After a suitable time portion 12b is withdrawn by pulling on portion 12a which still protrudes from the mouth. As portion 12b is retrieved, friction against the gastric walls and against the lower oesophageal sphinter 28 causes the protective sheath 22 to fully deploy, while portion 12b is held in place such that the protective sheath 22 envelops it.

Accordingly, as the protective sheath 22 and portion 12b are retrieved through the oesophagus, the mucus laden portion 12b is enclosed within the protective sheath 22 with the open end of the protective sheath 26 distally near the weight 16. Upon retrieving portion 12b, the ends of the protective sheath 22 are clamped thus sealing the gastric mucus and portion 12b within the protective sheath 22. The external parts of the protective sheath 22 can then washed before it is opened, portion 12b retrieved and cultured in the normal fashion for gastric mucosal biopsy or mucus specimen. Alternatively, a needle and syringe could be used to pierce the protective sheath 22, irrigate the inside with sterile saline, and aspirate the resuspended material with subsequent spinning and culture.

Figure 4:
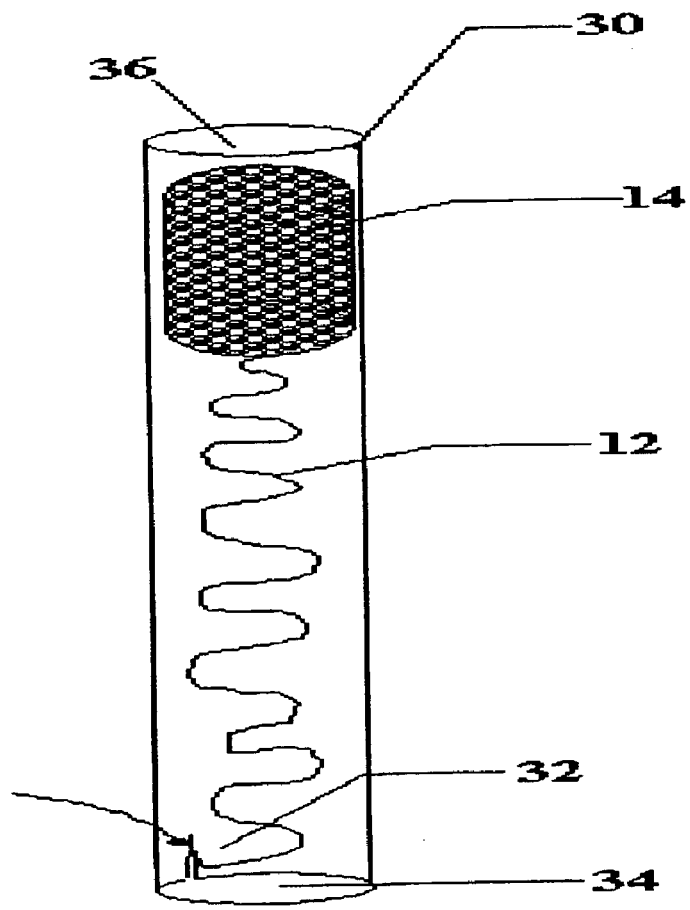
FIG. 4 shows the gastrointestinal sampling device loaded into a straw.

In a further preferred embodiment, the capsule 14 is placed in the end of a tube 30, for example a large polythene drinking tube or straw, and the drag material 12 is laid in the tube 30 behind the capsule 14 with 30 cm of the drag material 12 removed from the capsule 14. This is depicted in FIG. 4. It is evident from this design that there is no need for the drag material 12 to actually be rolled up inside the capsule 14 except for the piece which needs to open up inside the stomach. The end of the tube 30 away from the patient's mouth has a slit 32 into which the drag material 12 can be placed and held by tying a knot.

In FIG. 4 it can be seen that, in use, the tube has two ends, namely, a "drag material end" 34 and a "capsule end" 36. To swallow the capsule 14 after it has been loaded into the tube 30, the drag material end 34 is placed into a suitable drink, for instance a slightly acidic fruit juice drink or a carbonated drink, and the patient places the capsule end 36 of the tube 30 into his/her mouth. The patient then drinks the beverage in the normal fashion, during which time the capsule 14 is sucked from the end of the tube 30 with the column of liquid and ingested with minimal fuss. The device then operates in a similar fashion to that already described above.

The invention will now be further described by way of reference only to the following non-limiting examples. It should be understood, however, that the examples following are illustrative only, and should not be taken in any way as a restriction on the generality of the invention described above.

EXAMPLE 1

Types of Capsules

In all of the Examples described below the control string device used was the Enterotest capsule (HDC Corporation, San Jose, Calif.) that is routinely used for obtaining intestinal mucus from patients.

The Enterotest capsule is a string device comprised of a 90–140 cm long nylon fibre coated with a mixture of bee's wax and mineral oil enclosed in a 2.5 cm long weighted gelatine pharmaceutical capsule. In use, the string end protruding from the capsule is held and the capsule swallowed with a 100 ml of water. The gelatine capsule dissolves in the stomach acid, releasing the weight and sampling string. After 1 h, the string is pulled out through the mouth and oesophagus. The mucus clinging to the distal end is scraped off and examined as desired.

As described previously, the preferable capsules for this invention are either dissolvable gelatine pharmaceutical capsules comprising of two portions that readily dissolve within 5 minutes on entering a warm moist environment, or alternatively, non-dissolvable capsules made from gelatine capsules coated with non-toxic material that readily passes through the digestive system. The non-dissolvable capsules were made by coating the gelatine capsules with enamel, porcelain or latex rubber solutions by either dipping the capsule into the medium or applying a fine coat over the surface of the capsule using a brush and air-drying at room temperature. Only the larger part of the capsule was coated with the solution. The smaller base cap of the gelatine capsule was fitted over the dried-coated capsule to enclose the drag material and protective sheath device. Coating of one part of the capsule enabled the capsule device to separate in vivo when the gelatine portion dissolved thereby allowing the drag material to be released.

The enamel-coated gelatine capsule when dried to a translucent colour was of similar texture and flexibility as the uncoated gelatine capsule. In contrast, the porcelain-coated capsule was as hard as glass and just as fragile. Whereas, coating with the latex rubber solution resulted in the softening of the gelatine capsule mould yielding a flexible, rubbery capsule.

The solubility of the capsules was assessed visually in vitro by placing a lead weight inside the capsule and dropping the device in warm water for 1 hour. Within 5 minutes, the uncoated part of the capsule (ie the gelatine base cap) had dissolved and released the weight. After 1 hour at 37° C., both capsules coated with enamel or latex rubber remained intact in their moulded forms. Two types of insoluble capsules were developed: one that was as flexible as rubber and the other firm, but flexible like plastic. Unfortunately, the material on the porcelain-coated capsules dissolved immediately when immersed in warm water. This was visually noted by the release of white particles into the surrounding medium and collapse of the capsule.

EXAMPLE 2

Types of Drag Material

The absorptive nature of various types of drag material were assessed in vitro to determine their potential use as a sampling material for obtaining biological specimens from the gastrointestinal tract. The drag material samples selected encompassed both natural and synthetic fibres of different thicknesses (ply) and weaves. Attachment of *H. pylori* was measured as urease activity via a alkalimetric assay.

An alkalimetric assay for the enzyme urea amidohydrolase (urease) was used to compare the amount of *H. pylori* present on a drag material sample. Addition of urease to an assay mix of urea and phenol red in a 1.5 ml capacity disposable plastic cuvette results in the conversion of urea to ammonia and carbon dioxide. Ammonia increases the pH of the assay mix causing a colour change in the pH sensitive marker, phenol red that is monitored spectrally at a wavelength of 559.

The activity of the urease enzyme produced by the bacteria in a 50 µl aliquot of the sample was monitored using a Shimadzu UV 1601 spectrophotometer by observing the increase in absorbance at a wavelength of 559 nm over a period of 20 minutes against a reference cuvette. The increase in absorbance resulting from the activity of the urease enzyme is proportional to the amount of *H. pylori* present. An increase in the activity of urease in a sample would indicate an increase in the amount of *H. pylori* adhering to the drag material.

Figure 5:
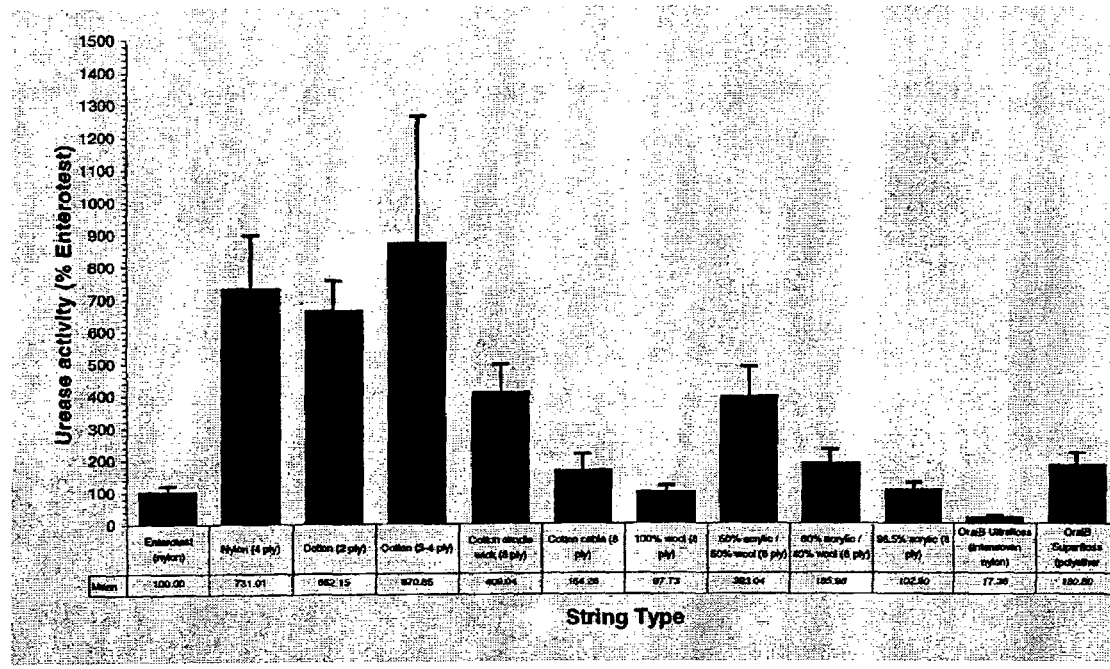
FIG. 5 shows the urease activity on drag material after 30 min incubation in a suspension of *H. pylori* on blood agar plates. Results are expressed as a percentage of the urease activity of the Enterotest string (mean± SEM of at least 3 samples).

All of the drag material samples tested, with the exception of the interwoven nylon (Oral B Ultrafloss), showed similar or better absorption of *H. pylori* compared to the Enterotest string. FIG. 5 shows that three of the drag materials (4 ply nylon, 2 and 3 ply cotton) yielded urease activity which was over 600% of the standard Enterotest string (control) indicating more *H. pylori* adhering to the surface of these drag materials. Absorption of *H. pylori* to drag material samples consisting of only wool or acrylic was similar to the control Enterotest string. Interestingly, samples consisting of a blend of both wool and acrylic showed better absorption of *H. pylori* as indicated by the increase in urease activity of the samples (50% wool/50% acrylic: 393.0%±95.6; 40% wool/60% acrylic: 186.0%±47.4).

The thickness and type of weave of the drag material was assessed for their contribution to the adherence of the bacteria to the material. Unexpectedly, the thicker samples of drag material (8 ply vs 2–4 ply) were less efficient at absorbing the bacteria, but were still far better than the Enterotest string (FIG. 5). Both the 2 ply (662.2%±95.2, n=12) and 4 ply (870.8%±392.6, n=3) cotton drag material samples were superior to the 8 ply cotton candlewick (409.0%±87.6, n=3), or cotton cable (164.3%±53.6, n=3). Similarly, a 4 ply nylon string sample showed a 731.0%±167.6 (6) compared to the nylon sample string of the Enterotest capsule (100.0%±20.6). One advantage of using a thinner drag material would be packaging of the device into smaller capsules, thereby making it easier to swallow. With regards to the present invention, a thinner sampling string would provide more available space within the existing capsule for the addition of other devices to protect the string from contamination (eg protective sheath device).

The differences in adherence of *H. pylori* to the different string samples may be due to the weave and treatment/coating of the material rather than the thickness of the fibre. The loosely woven 4-ply nylon string sample was significantly superior in absorbing *H. pylori* compared to the interwoven nylon from the OralB Ultrafloss sample string. Similarly, the 2 or 4-ply cotton material consisting of loosely woven fibres also demonstrated an enhancement in *H. pylori* binding compared to the tightly woven candlewick or cable. The results clearly indicate that the weave of the drag material is an important factor in the device for collection of microorganisms from the gastric juices.

A 50:50 mix of wool to acrylic resulted in a 4-fold increase in *H. pylori* attachment compared to the wool sample alone. However, an increased ratio of acrylic to wool (60%:40%) in the sampling material reduced urease activity (186%±47.4, n=6) compared to the 50:50 wool/acrylic mix (393.0%±95.6, n=11). It is possible that the acrylic material may act as a spacer allowing more surface area of the wool to be exposed for bacterial adherence. The acrylic material may be physically exposing the fibres of the wool to the bacteria or alternatively the combination of wool and acrylic may result in a charged environment that could potentially enhance the attachment of the bacteria.

The existing Enterotest device could be significantly improved by replacing the sampling material with a more absorptive material, thereby greatly enhancing the retrieval of microorganisms from the gastric fluid. Several drag materials of similar or lesser thickness to the Enterotest string demonstrated superior binding of *H. pylori*. These drag materials included natural (eg. cotton, wool) and synthetic materials (eg. nylon, polyether, polyamide) any of which could potentially replace the Enterotest string. A combination of natural and synthetic materials could also be used in the present invention to increase the collection of microorganisms on the drag material.

EXAMPLE 3

Coating of Drag Material

Surprisingly, nylon string of similar thickness and weave to the standard nylon fibre in the Enterotest capsule demonstrated superior adhesion of *H. pylori* on the drag material compared to the control (Enterotest) string (731.0%±167.6, n=6). During our initial testing using the Enterotest string it was noted that after 30 minutes exposure to a bacterial suspension of *H. pylori* some areas of the sampling material appeared dry and impermeable. We concluded that the addition of bee's wax and mineral oil to the Enterotest string may have been inhibiting the permeability of the string to the bacterial suspension. We therefore decided to treat the drag material to increase its absorptive nature. We concluded that compounds that react with sites found on the surface of bacteria could potentially enhance the binding and retrieval of microorganisms from gastrointestinal fluid samples.

Figure 6:
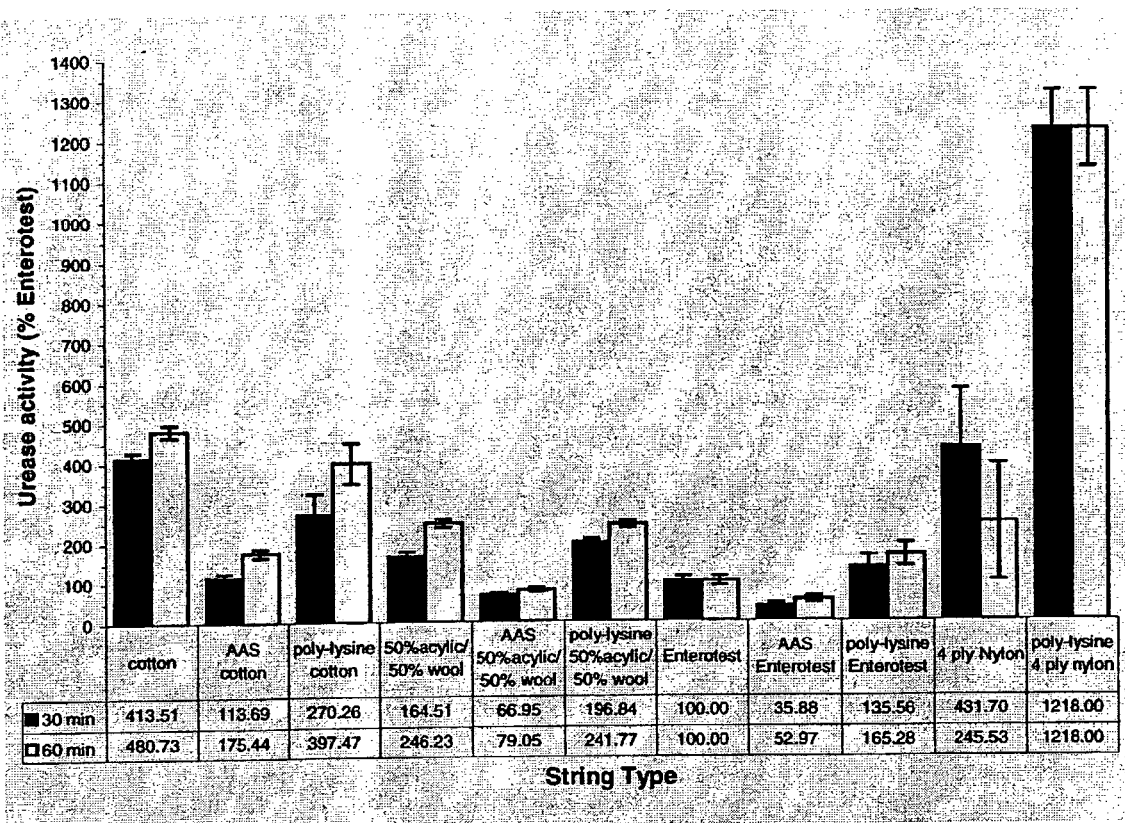
FIG. 6 shows the urease activity on drag material after 30 or 60 min exposure to a suspension of *H. pylori* on blood agar plates. Drag material samples were pre-treated with 3-aminopropyltriethoxysilane (AAS) or poly-L lysine prior to exposure to the bacteria. Results are expressed as a percentage of the urease activity of the Enterotest string (mean±SEM; n=3).

To address this avenue, drag material samples were pretreated with 3-aminopropyltriethoxysilane (AAS) or poly-L lysine (FIG. 6). These chemicals have been demonstrated to enhance the adhesion of biological material on treated slides. They were also selected on the basis of their availability and cost. Both compounds could potentially react with specific sites found on the surface of bacteria.

Coating the drag material with AAS was accomplished by submerging the drag material in a freshly made solution of 2% AAS (w/v) in acetone for 10 seconds. This was followed by two quick washes in acetone alone. The procedure was repeated once more before drying the drag material on a piece of Whatmann filter paper at 4° C.

A variety of natural and synthetic drag material samples were coated in AAS and dragged through a bacterial suspension of *H. pylori*. Treatment with AAS significantly reduced the adherence of *H. pylori* to the drag material as measured by the amount of urease activity in the sample collected (FIG. 6). In all cases, regardless of whether the material was natural or synthetic, the detected urease activity was approximately 50% less than the corresponding untreated drag material. AAS also failed to increase *H.*

*pylori* binding to the drag material sample when the exposure time to the bacteria was increased to 60 minutes.

Poly-L-lysine was also used to coat the drag material. Typically, a 0.01 to 0.1% solution, but ideally 0.1% of poly-L-lysine was used. Drag material was soaked in this for 10–60 minutes then allowed to dry before assembly.

Treatment of the drag material with poly-L-lysine also affected the binding of *H. pylori* to the sample (FIG. 6). Unlike the treatment with AAS, the absorption of the bacteria to the poly-L-lysine drag material sample depended on the material. The Enterotest drag material treated with poly-L-lysine showed some increase in adhering *H. pylori* to 135.6%±28.5 of the untreated control Enterotest drag material. The enhanced binding of the bacteria to poly-L-lysine treated nylon was further demonstrated on a 4 ply nylon string where the increase in urease activity reached over 1000% of the Enterotest drag material. The superiority of this drag material for collection of bacteria over the Enterotest makes it a prime candidate as a sampling drag material for the present invention.

In contrast, cotton treated with poly-L-lysine showed a decrease in *H. pylori* binding from 413.5%±15.3 to 270.3%±50.9. Whereas, the 50:50 blend of wool and acrylic treated with poly-L-lysine showed no change in the number of *H. pylori* absorbed on the sample material. However, the reduced urease activity of the poly-L-lysine treated cotton or wool/acrylic blend was still better than the normal or treated Enterotest string. Hence, these drag material samples cannot be discounted as potential sampling material for the present device.

EXAMPLE 4

Time Course Comparison of Drag Material

As noted in Example 3, after 30 minutes exposure, some areas of the sampling string appeared dry and impermeable to the suspension of *H. pylori*. A time course analysis was performed to evaluate the effect of exposure time on retrieval of a bacterial sample from different drag material samples.

Different types of drag materials were exposed to a bacterial slurry of *H. pylori* for up to 60 min on blood agar plates. The adherence of *H. pylori* to the Enterotest string was shown to be maximal after 10 minutes exposure with no further increase in *H. pylori* absorbance to the material after 60 minutes. In contrast, the 2 ply nylon and the 50:50 blend of wool and acrylic showed increased absorbance of the bacteria with time, up to 30 min. These materials showed enhanced retrieval of *H. pylori*, compared to the Enterotest, at all time points (1–60 min). Cotton cable showed a similar profile to the Enterotest string.

EXAMPLE 5

Weights Used for Drag Material Deployment

The weight 16 shown in FIG. 1 was used to assist in the deployment of the drag material once the capsule dissolved or separated. The weight in use enhanced the sampling of bacteria from under the gastric mucus by promoting the dragging of the drag material against the inner lining of the stomach. As shown in FIG. 1, the terminal end of the drag material, i.e. the end not attached to portion 12*a*, is attached to the weight. The weight can be permanently or detachably fixed to the drag material and may be constructed of any suitable material of any size. Ideally, the weight should be made of non-toxic material or metal that can be passed through the patient's stool when detached. Alternatively, it may be retracted with the sampling device.

Prior gastric string devices generally use a detachable stainless steel weight for the deployment of the sampling string. However, when the string is pulled from the stomach, the steel ball often comes into contact with the gastrointestinal sphincter causing discomfort to the patient, and in some cases, causing damage. To overcome this problem we have tried using a weight made of dissolvable or digestible materials such as sugared candy or chocolate. The weight promotes the dragging of the drag material against the inner lining of the stomach while it is slowly being digested by the gastric juices in the stomach. By the time the drag material is retrieved the weight should have been completely dissolved by the gastric juices. Even if the weight had not dissolved completely, the amount remaining on the end of the drag material should cause little discomfort or damage when passing through the gastrointestinal sphincter.

We assessed the action of the digestible weights in the deployment of the sampling material. Edible candy or chocolate was moulded into a ball to fit into the cap of a size 00 gelatine capsule. The drag material was attached to the moulded weights using dissolvable adhesive substances such as sugar water, honey, icing sugar or chocolate. Attachment of the drag material to the weight was achieved by either placing the drag material in the capsule with the weight on top and adding a drop of the adhesive material. Alternatively, we tried coating the end of the drag material with adhesive material and wrapping it around the weight before placing into the capsule. The weight and drag material were introduced into the capsule with a portion of the drag material exposed through the hole or perforation.

The weighted capsule attached to the drag material was lowered into a cylinder of warm water and held in place using a rod balanced on the top of the cylinder. Within 5 minutes, the gelatine capsule had dissolved and released the weighted device below the initial graduation mark. Unfortunately, the adhesive materials, with the exception of chocolate, dissolved within 5 minutes of exposure to the warm environment resulting in the release of the digestible weights from the drag material. Sugar water, honey or icing sugar would be unsuitable materials for the attachment of the weight to the drag material and should only be used on parts which require rapid release of the device.

Both the chocolate and sugared candy moulded material showed potential as dissolvable weights. When placed into warm water, the sugared candy dissolved faster than the weight made of chocolate. By 30 minutes, the weight made of sugared candy was reduced to approximately 50% of its original size whilst still maintaining a hard consistency. In contrast, approximately 25% the chocolate weight had dissolved after 30 minutes, but had a softer malleable consistency. Encouragingly, both digestible weights had dissolved completely after 1 hour.

Although the moulded candy or chocolate does not have the mass of a steel ball, they still were able to deliver the capsule device through the patient's oesophagus into the stomach. This was demonstrated in house by the swallowing a prototype containing the digestible weight and observing the yellow-stained mucus adhering to the sampling material when removed.

EXAMPLE 6

Sheath Material

One of the major problems that the prior art devices do not solve is the problem of bacterial contamination of the sampling string on removal of the gastrointestinal tract. Accordingly, we have investigated the use of a protective sheath 22 (FIG. 1). The protective sheath may be made of any suitable material, including plastic (eg. polyethylene or polythene film), cloth or finely knitted metal.

The basic prototype we tried comprised of a size 00 pharmaceutical gelatine capsule containing 120 cm nylon string as the drag material with a lead weight attached to one end, a protective sheath approximately 10 cm in length and 2.5 cm in width, and a protective sheath retainer. FIG. 2 shows a diagrammatic view of the protective sheath in its extended form. Three edges of the protective sheath were sealed to form an open-ended tube eg. dialysis tubing. The sheath retainer consisted of small plastic cylinder threaded halfway down the drag material and secured fast with adhesive. A simple knot would have sufficed just as well in preventing the drag material from being pulled through the holes on the capsule and sheath.

The free end of the drag material was threaded through the open-ended section of the protective sheath and out of the perforation at the top. The drag material was then threaded through a hole at the top of the largest part of the capsule so that the closed end of the protective sheath was within the capsule and in close proximity to the hole of the capsule. A round, hollow cylinder was then placed within the sheath by passing the weighted end of the drag material through the cylinder. A second hollow cylinder, one larger than the first, was passed over the smaller cylinder and used to push the sheath into the capsule. The smaller cylinder prevented the drag material from being packed inside the sheath while the larger cylinder was used to pack the sheath into the capsule. In this manner, only the sheath would be contained in the part of the capsule closest to the hole (where the retrieval drag material protrudes) and furthest to the weight. Alternatively, the sheath was packed into the capsule by removing the second cylinder and using a small pair of curved forceps to push the sheath down into the capsule. The procedure was made easier if the drag material was held taut and the cylinder held firm. The drag material and weight was then packed onto the protective sheath in the capsule and enclosed using the base part of the capsule.

EXAMPLE 7

Deployment of Protective Sheath

Several proto-types of the protective sheath device were produced and tested to assess the best type of sheath suitable for the device. The protective sheaths tested were made of synthetic materials such as sonic welded plastic film, or cloth (silk, chiffon, poly-sheen, nylon) and were all 10 cm in length but of varying widths with the sides and top sealed to form an open-ended tube. To evaluate the deployment of various types of sheath from the capsule, prototypes containing the different materials were assessed in warm water for the time taken for the deployment of the sheath.

After 5 minutes in warm water, the gelatine capsule had dissolved to release the sampling material and weight. Unfortunately, none of the protective sheaths tested extended to its full length to cover the sampling material after 1 hour in water (37° C.). This may have been due to residual gelatine remaining on the side of the outer sheath material. The maximum length deployed by any of the sheath devices assessed was 2 cm. Surprisingly, in 50% of the cases, the largest width plastic sheath would deploy to full length but only when the sheath was packed on the day and when the device was removed from the water. This would suggest the material needed to be more springy to move from the retracted position to an extended position.

We concluded that to encourage the extension of the sheath device a spring, or similar device was required. Two types of materials were used for the spring device, a nylon line and a Teflon coated stainless steel thread of equal diameter (0.5–2 mm). The spring device was attached with adhesive to the inner surface of the sheath device down one side of the sheath or down both sides forming a U shape and packed into the capsule in a similar manner as before. The spring device made of nylon proved to be the most successful prototype so far with a maximum deployment length of 3 cm after 1 hour in water. Complete deployment of the sheath device around the drag material may be achieved in vivo with peristalsis of the gut, or friction against the gastric wall or by catching against the lower oesophageal sphincter as it is removed.

An alternative version to the above device used a second non-absorbent fine string filament. One end was attached to the detachable weight and the other to the opening of the sheathe As the weight detached from the drag material, the second thread, still attached to the weight, was pulled down by the weight resulting in the extension of the sheath over the drag material.

Figure 7:
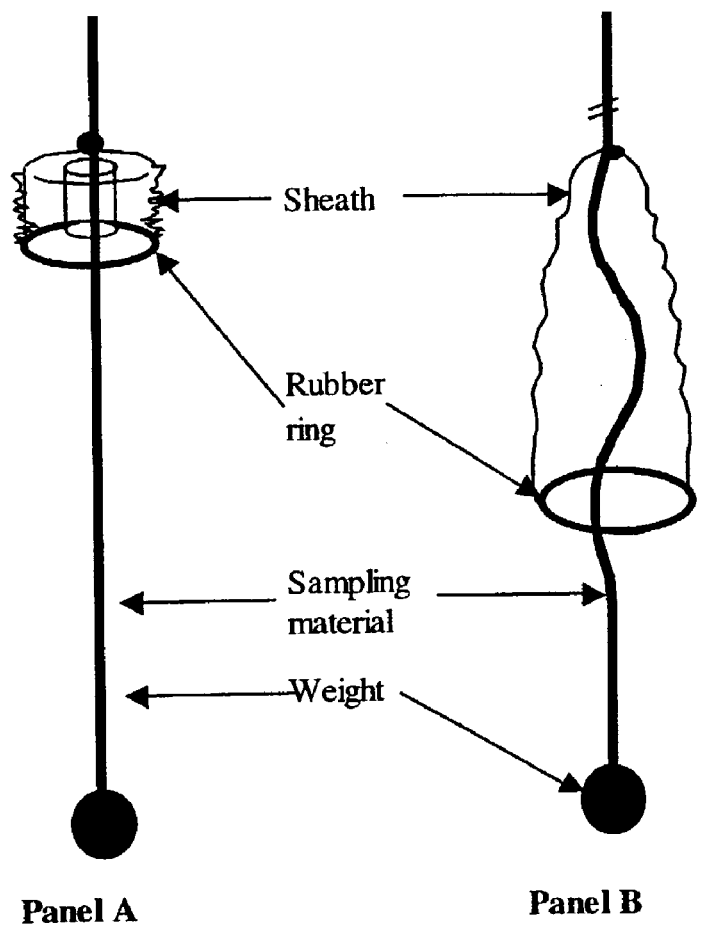
FIG. 7 shows a device comprising a rubber ring. Panel A shows the capsule dissolved, the drag material deployed and the protective sheath retracted. Panel B shows the device being removed with the protective sheath deployed such that it encases the drag material.

An alternative version to the above device used a rubber ring of similar diameter to the sheath (FIG. 7). As the string was withdrawn from the stomach, the rubber ring, attached to the opening of the sheath, deployed over the drag material by friction against the wall, thereby protecting the drag material from contamination as it passed through the mouth and oesophagus. The ring was reasonably rigid to allow the deployment of the sheath over the drag material, but flexible enough to pass through the oesophageal sphincter with moderate tension.

EXAMPLE 8

Stocking Device

Figure 8:
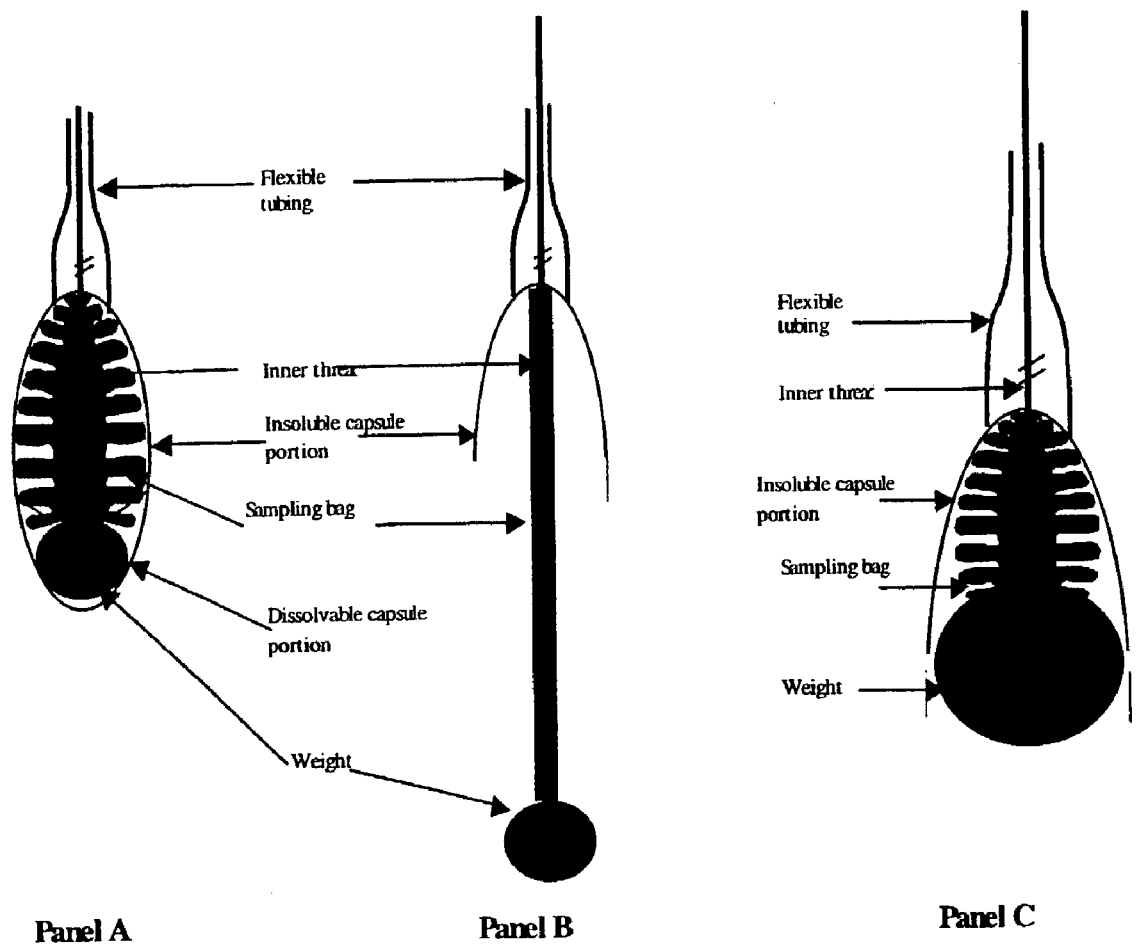
FIG. 8 illustrates the stocking device for obtaining gastrointestinal samples. Panel A shows the sac device in situ in the stomach before the capsule dissolves. Panel B shows the capsule dissolved and the sheath-like sac deployed. Panel C shows the device being removed with the sheath-like sac retracted such that it is encased in a protective collection reservoir.

FIG. 8 shows a device used in our trials. The deveice consisted of a capsule 14 comprising of two parts 14a and 14b. The capsule portion 14a consisted of an insoluble material that acted as a protective collection reservoir for gastrointestinal sample. Portion 14b of the capsule, constructed from gelatine, dissolved in the stomach and released the weighted drag material into the gastric environment of the stomach. Connected to the hole or perforation of the capsule was a thin, flexible tubing such as a fine line silastic catheter used in hospitals or other tubing of similar size and flexibility eg. 0.5–2 mm outside diameter. Through the tubing, a thread (typically comprising of nylon or Teflon coated stainless steel) was inserted, running through the hole or perforation into the capsule. The thread may or may not have a detachable weight attached to the end and any type of material would be used as long as it is firm but flexible enough to be pulled in and out of the tubing. Contained inside the capsule was a sheath-like sampling material that completely enclosed the flexible thread to form a sac. Potentially, the sac may contain devices that could aid in the collection or diagnosis of specific gastric pathogens.

In one embodiment of such a device, urease detection granules can be included within the sac. In this way, in a typical form of such granules, a colour change from yellow to red would indicate urease, a marker for a gastric infection (urease detection granules are the subject of U.S. Pat. No.5,314,804 issued May 24, 1994).

In use as the capsule is swallowed it pulls the tubing down the oesophagus into the stomach with it. Within approximately 5 minutes of entering the stomach, the warm moist environment of the stomach dissolves the gelatine part of the capsule 14b, leaving behind the insoluble top component of the capsule. At that time, the sampling sheath can be deployed by the action of the inner thread passing or being pushed down the tubing. By moving the flexible thread back and forth through the tubing the drag material comes into intimate contact with the adjacent mucus lining of the stomach. The extension of the sampling sheath results in scraping of the inner lining of the stomach, thereby enhancing the collection of microorganisms that live under the gastric mucus and between the epithelial cells of the stomach.

After a suitable indwelling period (typically 5–60 minutes), portion 12b is withdrawn into the insoluble part of the capsule 14a by pulling on the flexible thread device. This indwelling period could be substantially decreased since the present invention promotes scraping of the inner wall of the stomach. The device can be withdrawn by pulling on the tubing protruding from the mouth. As the capsule and sampling material are retrieved through the oesophagus, the mucus laden portion is enclosed within the protective collection reservoir (upper insoluble half of the capsule) by the weight or a similar plugging device (FIG. 5C). To reduce oral and oesophageal contamination, the external part of the capsule can be washed before it is opened to retrieve the sampling material The mucus specimen collected can then be cultured in the normal fashion and analysed for gastric pathogens. Alternatively, a needle and syringe could be used to pierce the protective collection reservoir, irrigate the inside with sterile saline, and aspirate the material for subsequent culture.

Initially, the patient may experience some discomfort or irritation in the pharynx or the feeling of a need to gag when the device is swallowed. However, this can be overcome by the use of topical anaesthetic agents such as viscous lidocaine (Xylocalne) or throat lozenges to numb the irritation associated with the device.

EXAMPLE 9

Straw Device

Figure 9:
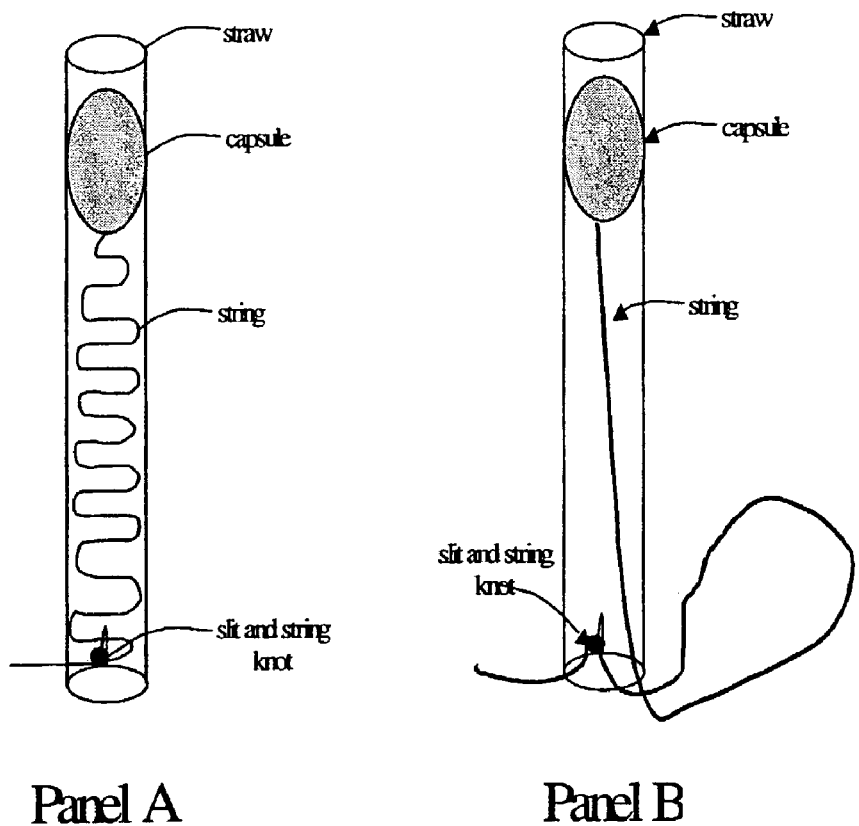
FIG. 9 shows a polythene cylinder or straw device.

As described previously, in order to aid the swallowing device, a straw or take may be used. The device illustrated in FIG. 9 comprises of a polythene cylinder, a capsule containing the sampling material with or without the protective sheath and a retrieval string attached to the sampling material in the capsule. The loose end of the retrieval string is secured to the polythene cylinder by a knot inserted into a slit at one end and the remaining exposed length of the string packed loosely or coiled in the inner compartment of the cylinder (FIG. 9A). Preferably the capsule is located at the opposite end of the cylinder from the slit and knot so as to prevent the retrieval string from blocking the passage of the capsule as it is swallowed.

In an alternative embodiment, the capsule is loaded into the straw whereas the filament or tubing is coiled loosely outside the straw (FIG. 9B). To swallow the device, the coils are allowed to float within the drink and are sucked up as the capsule is swallowed. In this version a "pom-pom" or other soft expansion of the filament prevents it from passing through the straw and being swallowed.

The fasted patient swallows the string and capsule device through the cylinder while drinking a "diet cola". The column of liquid forces the capsule and string down the oesophagus and into the stomach pulling the retrieval string until it is extended to its full length.

Alternatively, an acidic fruit juice drink reconstituted from a dry powder could be used. Some such drinks have quite a low pH which would inhibit commensal flora but would not harm H. pylori.

The cylinder used in this device was 20 cm in length and 1.25 cm in diameter. This allowed even the larger sized capsules to be easily swallowed. The inclusion of such a device with the present invention would greatly improve the ease of swallowing the device.

EXAMPLE 10

Coating of Drag Material with a pH Sensitive Indicator

In an enhanced version of the device, litmus (pH indicator) is incorporated into the drag material. Alternatively, the "urease detection granules" (U.S. Pat. No. 5,314,804 issued May 24, 1994) can be attached to the drag material and observed for colour change after retrieval. Typically, such beads can indicate both pH and the presence of urease. This would allow portions of the string with large numbers of attached H. pylori to be selected for more fastidious culture methods.

The pH of secretions obtained by the test can be used as a guide to identify the location of the sampling prior to culturing the microorganism. When the device is withdrawn through the mouth, the pH of the mucus adhering to the terminal portion of the drag material is tested. An acid pH would indicate a gastric source of sampling by the drag material. In most cases, finding of yellow-staining bile on the distal end of the drag material correlates with the presence of bile in the duodenal lumen and is used as an additional indicator of a duodenal site of sampling.

The Enterotest capsule uses a simple pH indicator stick included in the packaging to identify the location of the string sampling. Unfortunately, high gastric pH and/or contamination of the string test on withdrawal with alkaline saliva may result in a false reading. The specificity of the test would be greatly increased if the pH of the mucus adhering to the string could be controlled and protected from contamination. One of the embodiments of the present invention incorporates a pH sensitive marker within the device. The pH sensitive marker can be incorporated into the drag material, or within the capsule or weight material.

A preliminary test of the present invention for the inclusion of a pH marker on the drag material was undertaken. Three pH sensitive markers were utilised in this study, phenol red, bromothymol blue and anthocyanin. The pH markers were incorporated onto the drag material by absorption of the dye material after submersion in an alcohol or water based solution containing the dye material and then air-drying the drag material. When dried, the dyed material was subjected to solutions of different pH to assess the range of colour obtained with the different dye material.

Table 1 lists the colour changes observed at acidic, neutral or alkaline pH with the different dye material.

TABLE 1

| pH | Colour Change | | |
|---|---|---|---|
|  | Phenol Red | Bromothymol Blue | Anthocyanin |
| 2.0 (acidic) | Red | Brown | Pink |
| 7.0 (neutral) | Orange | Orange | Blue |
| 10.0 (alkaline) | Purple | Blue | Green |

Provision of a sensitive pH marker into the invention would allow the precise location of the mucus samples to be visually assessed by the colour change on the string material. The device would enable the clinician to identify samples from specific regions of the gastrointestinal tract and allow the retrieval and culturing of specific pathogens located in this region.

EXAMPLE 11

Viability of H. pylori Recovered from Drag Material

Culturing the organisms adhering to the drag material would allow the physician to diagnose certain gastrointestinal pathogens and test for their sensitivity to various drugs before prescribing antibiotic therapy.

Figure 10:
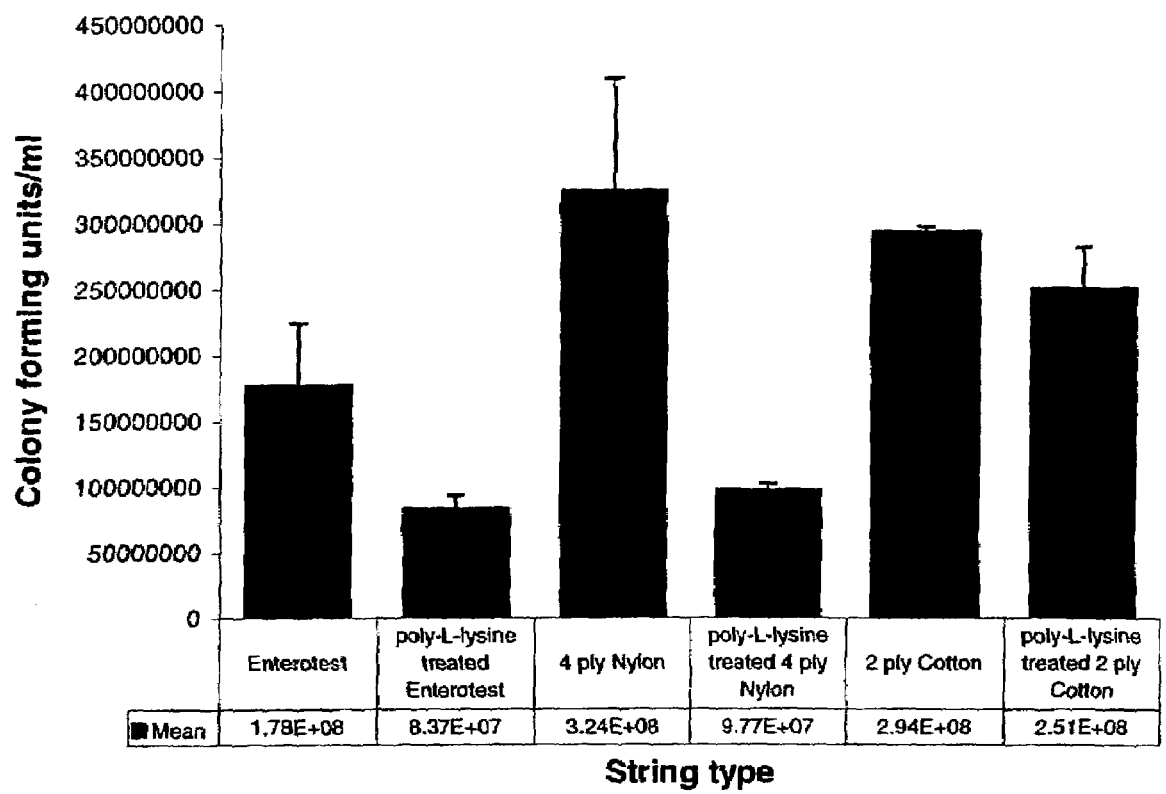
FIG. 10 shows the viability of *H. pylori* recovered from drag material. (mean±SEM; n=3).

A 60 cm piece of drag material was incubated in a suspension of H. pylori on blood agar plates after which a sample of the bacteria adhering to the drag material was cultured onto blood agar plates similar to the procedure used in the Enterotest. Quantitative cultures were then performed by ten-fold serial dilution of the samples, followed by streak plating the diluted suspension onto blood agar plates. The number of colony-forming units (c.f.u.) of H. pylori isolated from the drag material was compared to the Enterotest string (FIG. 10).

Viability of H. pylori after exposure to "diet cola" was also determined. Since the straw device described in Example 10 utilises diet cola as a medium for inducing the patient to swallow the device, the viability of H. pylori was assessed after exposure to the "diet cola". Aliquots were taken from a suspension of H. pylori after exposure to saline or "diet cola" and quantitative cultures were performed by ten-fold serial dilutions.

Figure 11:
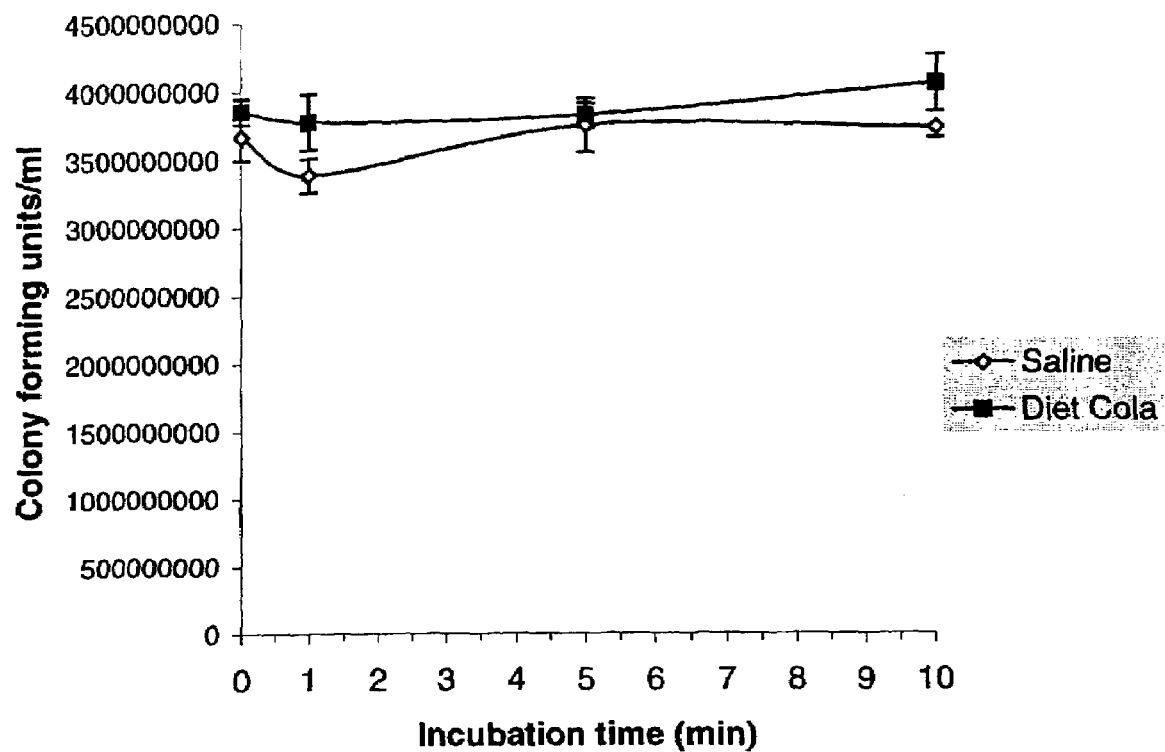
FIG. 11 demonstrates viability of *H. pylori* in culture after exposure to diet cola. (Mean±SEM, n=3)

FIG. 11 demonstrates that exposure to a medium of "diet cola" results in a decrease in the number of viable bacteria present in the medium. However, this effect was not specific to the "diet cola" since H. pylori in saline also showed a similar profile.

What is claimed is:

1. A gastrointestinal sampling device comprising:
    a malleable drag material for obtaining a gastrointestinal sample having a first portion and a second portion; and
    a deployable protective sheath for deployment from a packed position to an extended position about said first portion of said malleable drag material such that said first potion of said malleable drag material is substantially enclosed by said deployable protective sheath upon removal from the gastrointestinal tract, said second portion of said malleable drag material being exterior of said deployable protective sheath.

2. The device according to claim 1, wherein said device is used for the diagnosis of certain gastrointestinal pathogens.

3. The device according to claim 1, wherein said malleable drag material is selected from the group consisting of absorbent string, cotton, sampling cloth, wool, acrylic, nylon, plastic, chain links and finely woven metal or mixtures thereof.

4. The device according to claim 3, wherein said malleable drag material is 50% wool and 50% acrylic.

5. The device according to claim 1, wherein said malleable drag material is coated with a bacterial adherent.

6. The device according to claim 5, wherein the bacterial adherent is poly-L-lysine.

7. The device according to claim 1, wherein said malleable drag material further comprises a pH indicator or urease indicator.

8. The device according to claim 1, further comprising a capsule for carrying said malleable drag material and said deployable protective sheath.

9. The device according to claim 1, wherein said deployable protective sheath is deployed about said drag material by movement from said packed position to said extended position.

10. The device according to claim 9, wherein the packed position of said deployable protective sheath is held in place by edible glue.

11. The device according to claim 9, wherein said deployable protective sheath is assisted in deployment by the use of a spring device.

12. The device according to claim 11, wherein said spring device is a nylon line or a polytetrafluoroethylene coated stainless steel thread.

13. The device according to claim 11, wherein said spring device is attached with adhesive to the inner surface of said deployable protective sheath.

14. The device according to claim 1, further comprising a non-absorbent filament wherein one end of the filament is attached to one end of the deployable protective sheath, with the other end of the filament attached to a weight so that upon deployment the weight assists in the extension of said deployable protective sheath over said first portion of said malleable drag material.

15. The device according to claim 1, further comprising a rubber ring attached to said deployable protective sheath, wherein said rubber ring is of a similar diameter to said deployable protective sheath and said ring assists in the deployment of said deployable protective sheath.

16. The device according to claim 1, wherein said malleable drag material is folded within the capsule.

17. The device according to claim 1, further comprising a weight for assisting with the extension of said first portion of said malleable drag material in the stomach of a patient.

18. The device according to claim 17, wherein the weight is a dissolvable weight.

19. The device according to claim 8, wherein said capsule is constructed of a non-gelatine dissolvable material.

20. The device according to claim 8, wherein said capsule is no more than two centimeters in length.

21. The device according to claim 8, wherein said capsule is no more than 0.9 centimeters in diameter.

22. The device according to claim 8, wherein said capsule is non-dissolvable and is composed of at least two parts joined together with water-soluble glue.

23. A method of gastrointestinal sampling comprising the steps of:
    swallowing a gastrointestinal sampling device comprising a malleable drag material and deployable protective sheath;
    allowing sufficient time for said drag material to obtain said gastrointestinal sample;
    withdrawing said drag material such that on withdrawal said deployable protective sheath extends from a packed position to an extended position and encloses a portion of said drag material; and
    recovering said gastrointestinal sample for testing.

* * * * *